United States Patent [19]
Vysin et al.

[11] Patent Number: 4,870,578
[45] Date of Patent: Sep. 26, 1989

[54] DIASTOLIC CLAMP FOR BIOIMPEDANCE MEASURING DEVICE

[75] Inventors: Vlastimil P. Vysin, San Clemente; Bohumir Sramek, Irvine, both of Calif.

[73] Assignee: Bomed Medical Manufacturing, Ltd., Irvine, Calif.

[21] Appl. No.: 232,481

[22] Filed: Aug. 17, 1988

Related U.S. Application Data

[63] Continuation-in-part of Ser. No. 86,972, Aug. 19, 1987, abandoned.

[51] Int. Cl.$^4$ ................................................ A61B 5/04
[52] U.S. Cl. ........................... 364/413.05; 364/413.07; 128/693; 128/671
[58] Field of Search ...................... 364/413.07, 413.05; 128/671, 693, 709, 723, 708, 734

[56] References Cited

U.S. PATENT DOCUMENTS

| | | | |
|---|---|---|---|
| 3,976,052 | 8/1976 | Junginger et al. | 128/671 |
| 3,994,284 | 11/1976 | Voelker | 128/693 |
| 4,305,400 | 12/1981 | Logan | 128/670 |
| 4,422,458 | 12/1983 | Kravath | 128/671 |
| 4,450,527 | 5/1984 | Sramek | 364/413.07 |
| 4,676,253 | 6/1987 | Newman et al. | 128/693 |
| 4,757,824 | 7/1988 | Chaumet | 128/671 X |

OTHER PUBLICATIONS

W. G. Kubicek et al., "Development and Evaluation of an Impedance Cardiac System", *Aerospace Medicine*, vol. 9, Dec. 1966, pp. 1208–1212.

W. G. Kubicek et al., "The Minnesota Impedance Cardiograph–Theory and Applications", *Biomedical Engineering*, Sep. 1974, pp. 410–416.

Miyamoto, Y. et al., "Automatic Determination of Cardiac Output Using an Impedance Plethysmography", Biotelemetry Patient Monitoring, vol. 8, No. 4, 1981, pp. 189–203.

Miyamoto, Y. et al., "Automatic Determination of Cardiac Output by Impedance Plethysmography Under Various Conditions", *Proceeding of the VTH ICEBI*, Aug. 1981, Tokyo.

Sramek, B. Bo., "Noninvasive Technique for Measurement of Cardiac Output by Means of Electrical Impedance", *Proceedings of the VTH ICEBI*, Aug. 1981, Tokyo.

Sramek, B. Bo., "Cardiac Output by Electrical Impedance", *Medical Electronics*, Apr. 1982, pp. 93–97.

Sramek, B. Bo. et al., "Stroke Volume Equation With a Linear Base Impedance Model and Its Accuracy, As Compared to Thermodilution and Magnetic Flow Meter Techniques in Humans and Animals", *Proceedings of the VITH International Conference on Electrical Bioimpedance*, Zadar, Yugoslavia, 1983.

Sramek, B. Bo., "Electrical Bioimpedance", *Medical Electronics*, Apr. 1983, pp. 95-10-5.

Geddes, "The Measurement of Cardiac Output and Blood Flow", Chapter Four, *Cardiovascular Devices and Their Application*, John Wiley and Sons, New York, 1984, pp. 100–107 and 122–135.

Primary Examiner—Clark A. Jablon
Attorney, Agent, or Firm—Knobbe, Martens, Olson & Bear

[57] ABSTRACT

An electrical bioimpedance measuring device is used to measure changes in the electrical resistance of a segment of the thorax of a human body caused by changes in the blood perfusion in that segment resulting from the pumping action of the heart. The electrical resistance of also changes as a result of respiration, and the respiratory-induced changes are typically much larger than the cardiac-induced changes and cause large changes in the voltages in the measuring equipment. In order to suppress the large voltage changes, a clamping circuit is included that is synchronized with the electrical activity of the heart. The clamping circuit is timed to clamp the voltages in the measuring equipment to a baseline reference voltage in the time preceding the beginning of mechanical systole. The voltage clamping is released during the mechanical systole of the heart so that the changes in the voltages (i.e., the bioimpedance changes) caused by the pumping action of the heart during mechanical systole can be measured.

7 Claims, 8 Drawing Sheets

DIASTOLIC CLAMP FOR BIOIMPEDANCE MEASURING DEVICE

REFERENCE TO COPENDING APPLICATION

This application is a continuation-in-part of U.S. patent application Ser. No. 086,972, filed on Aug. 19, 1987 abandoned.

BACKGROUND OF THE INVENTION

1. Field of the Invention

The present invention relates to apparatus and methods for measuring the blood perfusion through various tissue segments of the human body. In particular, the invention relates to apparatus and methods to measure the electrical impedance of a segment of a human body caused by changes in the volume of blood in the segment.

2. Description of the Related Art

The electrical bioimpedance of a segment of a human body depends upon a number of factors, one of which is the quantity of blood and the conductivity of the blood. Measuring the electrical bioimpedance of the segment is a convenient means for non-invasively determining the blood perfusion of the various tissues in the segment. By measuring the magnitude of the unchanging components of the bioimpedance as well as the rate and amplitude of changes in the bioimpedance caused by blood flow generated by the pumping action of the heart, several important cardiac parameters can be calculated and used to determine the condition of the heart.

When measuring the electrical bioimpedance of a body segment, such as the thorax, the primary interest is in changes in the electrical bioimpedance caused by the periodic increases and decreases in the quantity of blood in the segment caused by the periodic pumping action of the heart. The thoracic area of the human body is typically the principal area where measurements of the cardiovascular bioimpedance occur because of the presence of large blood vessels that have significant changes in blood quantity throughout the cardiac cycle. However, changes in the thorax during respiration also cause changes in the electrical bioimpedance of the thorax and thus cause major difficulties in measuring the electrical bioimpedance of the cardiovascular activity in the thoracic area. The changes in the bioimpedance due to respiration are approximately an order of magnitude greater than the changes in electrical bioimpedance caused by the heart and are superimposed over the smaller cardiovascular bioimpedance changes to form a composite bioimpedance signal.

Some devices presently being used require voluntary apnea to take a measurement of the cardiovascular component of bioimpedance. However, this requirement of apnea makes it extremely difficult, if not impossible, to measure the cardiovascular bioimpedance in many instances. Often voluntary apnea cannot be performed because the person whose bioimpedance is being measured is unconscious, under anesthesia, or ill. Further, even when voluntary apnea may be performed the undisturbed cardiovascular electrical bioimpedance can be measured only for a short time.

Moreover, it is difficult, if not impossible, to completely separate the cardiovascular bioimpedance signals from the respiratory bioimpedance signals by using filtering. A common approach has been to use the first derivative of the composite of the bioimpedance signal. This reduces the magnitude of the problem because the derivative reduces the lower frequency/higher magnitude respiratory part of the bioimpedance signal. One such method, disclosed in U.S. Pat. No. 4,450,527, calculates and uses a sliding average of the maximum rate of impedance change over four heart beats to further offset the effects of respiratory bioimpedance. Even with the improved methods presently available, respiratory changes in the bioimpedance continue to interfere with the accurate measurement of cardiovascular bioimpedance.

SUMMARY OF THE INVENTION

The present invention includes an apparatus for non-invasively measuring the cardiac output of a patient through the use of a bioimpedance measuring device while advantageously suppressing or eliminating the unwanted effects of respiration. A typical bioimpedance measuring device comprises a high frequency, constant amplitude current source, the output of which is injected through a portion of the patient's body between a pair of current injecting electrodes. A pair of sensing electrodes senses the voltage across a second (inner) portion of the patient's body caused by the current flow in the first portion of the patient's body. The outputs of the voltage sensing electrodes are connected to an amplifier that provides an amplified electrical bioimpedance signal at its output. The electrical bioimpedance signal corresponds to the patient's thoracic impedance as a function of time. The bioimpedance measuring device further employs a differentiating circuit that differentiates the electrical bioimpedance signal in order to generate a differentiated electrical signal corresponding to the rate of change of thoracic impedance as a function of time. The apparatus of the present invention includes a circuit that periodically clamps the differentiated electrical signal so that the signal is active only for a predetermined time following the beginning of each cardiac cycle. The circuit advantageously suppresses or eliminates the unwanted effects of respiration on bioimpedance measurements by forcing the signal to begin from a baseline voltage at the beginning of each cardiac cycle.

In a preferred embodiment of the apparatus of the present invention, the clamping circuit comprises an electronic switch that is timed to be closed except during a predetermined time following the beginning of each cardiac cycle. The preferred embodiment of the clamping circuit also employs a coupling capacitor that is placed between the input of the clamping circuit and the source of the signal to be clamped. The invention further includes a clamping control circuit that is responsive to the patient's electro-cardiac signals so that the clamping control circuit is synchronized with the patient's cardiac cycle. The clamping control circuit provides an output signal that controls the closing of the electronic switch that comprises the clamping circuit. When the electronic switch is closed, the signal is clamped to a baseline voltage. When the switch is opened, the opposing voltage stored across the coupling capacitor forces the signal to start from that same baseline voltage. The effects of respiration on the electrical bioimpedance signal are thereby suppressed or eliminated since the respiratory contribution is typically of greater magnitude and lower frequency than the cardiac contribution.

In accordance with a preferred embodiment of the invention, the clamping circuit is located at the input of the differentiating circuit of the bioimpedance measuring device. In an alternative embodiment the clamping circuit and the coupling capacitor are placed at the output of the differentiating circuit. In either embodiment, the differentiated bioimpedance signal is clamped by the operation of the clamping circuit.

DETAILED DESCRIPTION OF THE PREFERRED EMBODIMENT

Figure 1:
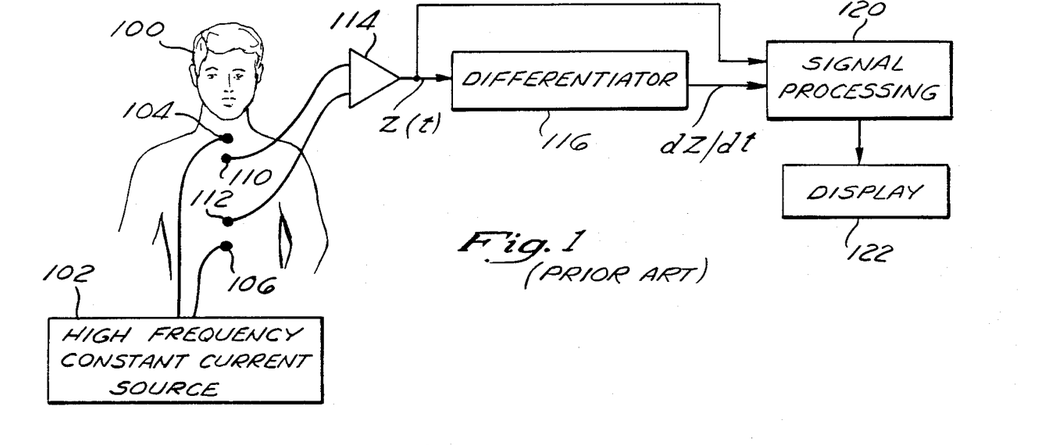
FIG. 1 is a block diagram illustrating the components of a typical bioimpedance measuring device.

FIG. 1 diagrammatically illustrates a typical apparatus for measuring the cardiac output of a patient 100. In order to obtain thoracic cardiovascular data, the output of a high frequency constant current source 102 is applied to a segment of the body of the patient 100 through a pair of current injecting electrodes 104 and 106, shown in FIG. 1 as a pair of spot electrodes. For example, in FIG. 1, the segment of the patient's body is the thorax. A voltage is generated across the body segment by the flow of the high frequency current through the tissues between the two current injecting electrodes 104 and 106. The voltage is proportional to the magnitude of the constant current and also proportional to the electrical bioimpedance of the tissues between the two current injecting electrodes 104 and 106. The voltage is detected by a pair of voltage sensing electrodes 110 and 112 located on the body segment between the two current injecting electrodes 104 and 106. It should be understood that in many applications, the injection of current and the sensing of voltage may be accomplished with an array of electrodes rather than with two pairs of electrodes as shown herein for simplicity. The appropriate placement of the electrode array, represented herein by the electrodes 104, 106, 110 and 112, is disclosed by U.S. Pat. No. 4,450,527, which is incorporated herein by reference.

The two sensing electrodes 110 and 112 are electrically connected to the input of a differential amplifier 114. The voltage detected by the sensing electrodes 110 and 112 is amplified by the differential amplifier 114 to produce an electrical bioimpedance signal Z(t) directly related to the bioimpedance of the patient's thorax as a function of time. This electrical bioimpedance signal Z(t) is then provided as an input to a differentiating circuit 116 that differentiates the Z(t) signal and produces a differentiated electrical signal dZ/dt that corresponds to the rate of change of thoracic impedance as a function of time. The electrical bioimpedance signal Z(t) and the differentiated electrical signal dZ/dt are provided as inputs to a signal processing circuit 120 that analyzes one or both of the signals and calculates cardiac parameters that correspond to changes in the electrical bioimpedance signal. The calculated parameters are communicated to an operator by a visual display 122 such as a video monitor, a printer, or the like.

Figure 2A:
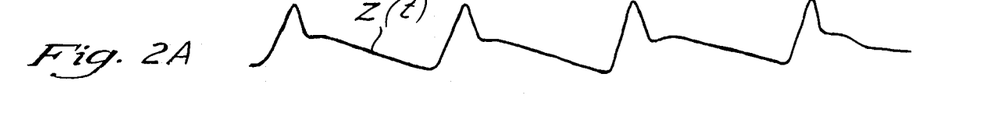
FIG. 2A is a graph of a typical electrical bioimpedance signal Z(t) caused by cardiac activity where the patient is participating in voluntary apnea.
Figure 2B:
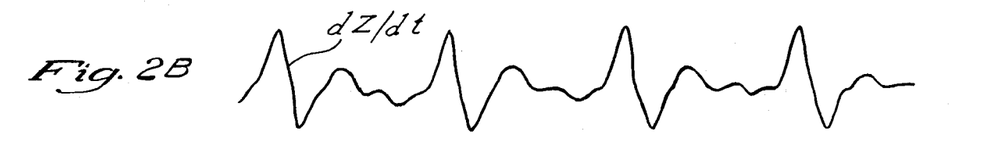
FIG. 2B is a graph of a differentiated electrical signal dZ/dt which is the derivative of the electrical bioimpedance signal Z(t) shown in FIG. 2A.

The operation of the exemplary bioimpedance measuring system of FIG. 1 can be understood by referring to FIGS. 2A and 2B which illustrate waveforms of exemplary electrical bioimpedance signals. FIG. 2A shows a typical voltage waveform generated by the differential amplifier 114 in FIG. 1 caused by cardiovascular activity where the patient is participating in voluntary apnea. Since the current applied to the body segment of the patient 100 in FIG. 1 is constant, the changes in the amplitude of the voltage generated by the differential amplifier correspond to changes in the electrical bioimpedance of the body segment caused by changes in the volume of blood in the segment throughout the cardiac cycle and is thus labelled as Z(t) in FIG. 2A. It should be understood that the waveform in FIG. 2A does not include the high frequency components of the detected voltage as such components are filtered out by the use of a conventional low-pass filter (not shown).

It should be understood that the increase in blood flow during the mechanical systole of the heart causes a decrease in the electrical bioimpedance of the thoracic area of the body. However, the differential amplifier 114 typically inverts the Z(t) signal so that the Z(t) signal is typically illustrated as shown in FIG. 2A with a positive-going transition corresponding to increased blood perfusion during mechanical systole. This convention is used on the illustrations of the electrical bioimpedance Z(t) throughout this specification.

FIG. 2B illustrates a voltage waveform corresponding to the differentiated electrical signal dZ/dt generated by the differentiator 116 of FIG. 1 and is thus the derivative of the electrical bioimpedance signal shown in FIG. 2A.

Figure 2C:
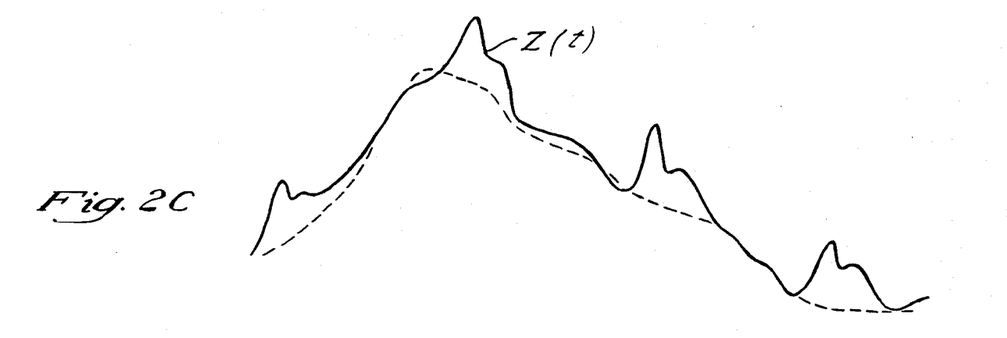
FIG. 2C is a graph of a typical electrical bioimpedance signal Z(t) modulated by the electrical bioimpedance signal caused by respiration (shown in dashed lines).
Figure 2D:
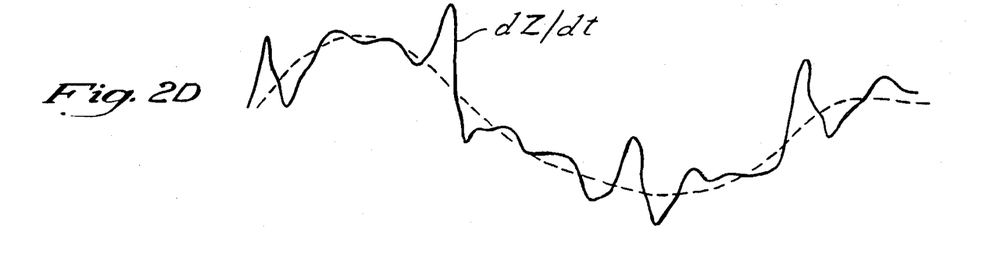
FIG. 2D is a differentiated electrical signal dZ/dt which is the derivative of the electrical bioimpedance signal Z(t) shown in FIG. 2C.

As set forth above, the signal waveforms illustrated in FIGS. 2A and 2B are idealized waveforms that assume that the patient is holding his or her breath (i.e., apnea). The ideal signals illustrated by FIGS. 2A and 2B are often not available since voluntary apnea is difficult, if not impossible, to accomplish by a patient who is ill or under anesthesia. The signal more commonly available at the output of the differential amplifier 114 is illustrated by FIG. 2C which illustrates the electrical bioimpedance signal Z(t) due to cardiac activity modulated by the electrical bioimpedance signal caused by respiratory activity (shown in dashed lines). It is desirable that changes in the electrical bioimpedance signal caused by the cardiovascular activity be isolated from those changes caused by respiration. Since the harmonic content of the that portion of the bioimpedance signal caused by respiration is relatively low in comparison to that portion of the bioimpedance signal caused by the systolic portion of the cardiac activity, it has been found that the signal-to-noise ratio of the cardiac-induced changes in electrical bioimpedance can be improved by differentiating the electrical bioimpedance signal Z(t) shown in FIG. 2C to obtain the differentiated electrical signal dZ/dt shown in FIG. 2D. However, it can be seen that the dZ/dt signal waveform in FIG. 2D comprises considerable variations in its amplitude caused by the changes in electrical bioimpedance caused by respiration.

While using the differentiated electrical signal reduces the magnitude of the respiration-induced problem, the problem still remains, particularly with respect to the determination of the maximum rate of impedance change as indicated by the maxima of the dZ/dt signal. Because the relative first harmonic frequencies of normal breathing and the heart are in approximately a 1 to 4 ratio, one method previously used to suppress the effects of respiration involved the calculation of a sliding average of the maximum rate of impedance change (the dZ/dt maxima) over four heartbeats. Such a method is disclosed in U.S. Pat. No. 4,450,527.

In addition to generating substantial unwanted excursions in the Z(t) and dZ/dt signals, as discussed above, the respiration-induced changes in the electrical bioimpedance signals tend to be large compared to the cardiac-induced changes in the electrical bioimpedance signals. As a result, the circuits used to differentiate and amplify the composite electrical bioimpedance signals are caused to operate over a larger range of input magnitudes than if the cardiac-induced electrical bioimpedance signal alone were differentiated and amplified.

The present invention provides a novel apparatus and method for substantially reducing or eliminating the effects of respiration in bioimpedance measurements by obtaining all the desired information during a time interval in each cardiac cycle corresponding to the mechanical systole of the heart. An important aspect of the present invention is the use of the electrocardiogram (ECG) signal to time the operation of a signal clamping circuit to be described below.

Figure 4:
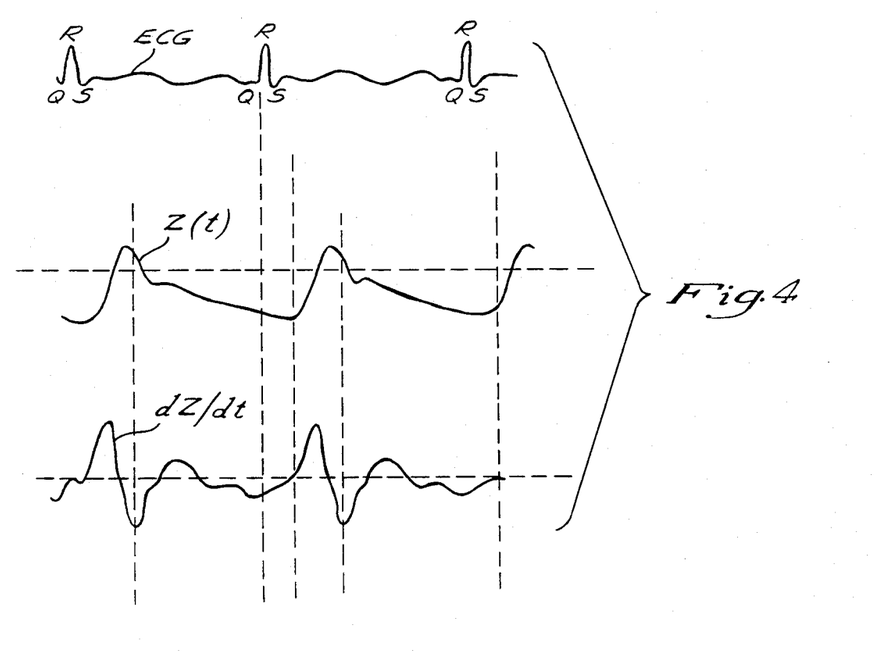
FIG. 4 is an illustration of the timing relationship that exists between a typical electrocardiogram signal, a typical electrical bioimpedance signal Z(t), and a typical differentiated electrical signal dZ/dt.

FIG. 4 illustrates the timing relationship between an electrocardiogram (ECG) signal of the patient's heartbeat, the electrical bioimpedance signal Z(t), and the differentiated signal dZ/dt. FIG. 4 further illustrates the relationship between the above signals and the Pre-Ejection Period (the PEP interval), the mechanical systole, and the mechanical diastole of the heart. Referring to FIG. 4, it can be seen that the commencement of the mechanical systole can be predicted by the occurrence of the QRS wave of the patient's electrocardiogram. The period of time between the onset of Q of the QRS complex and the commencement of the mechanical systole is referred to as the Pre-Ejection Period (PEP) of the heart and is typically greater than 40 mS. It can also be seen that the changes in electrical bioimpedance Z(t) and the corresponding changes in the differentiated electrical bioimpedance signal dz/dt caused by the increased flow of blood during mechanical systole do not occur until after the conclusion of the Pre-Ejection Period. Since the primary indication of the heart's ability to pump blood through the vascular system of the patient's body is the heart's ability to rapidly increase the quantity of blood in the descending aorta during mechanical systole, it is generally sufficient to analyze the electrical bioimpedance signal Z(t) and/or the differentiated electrical bioimpedance signal dZ/dt during the time corresponding to the mechanical systole of the heart. During the rest of the heart cycle, it is not necessary to analyze the fluctuations in the Z(t) and the dZ/dt signals. Thus, it has been found that these fluctuations in the signals can be suppressed without losing significant electrical bioimpedance information related to the cardiac output.

As will be described below, the present invention includes a clamping circuit having an electronic switch that is controlled by the QRS wave of the ECG signal of the patient's heart. The electrical bioimpedance signal Z(t) or the differentiated electrical bioimpedance signal dZ/dt is clamped in synchronization with the ECG signal so that the fluctuations in the clamped signal are suppressed prior to the beginning of the mechanical systole of the heart. Since it is only important that the signal be clamped prior to the beginning of the mechanical systole of the heart, the clamping of the Z(t) signal or the dZ/dt signal can begin as early as the end of the previous mechanical systole or begin as late as the occurrence of the preceding ECG Q-wave. Hence, the clamping has a minimum time duration approximately equal to the minimum PEP interval and has a maximum time duration approximately equal to the duration of the mechanical diastole.

Figure 3A:
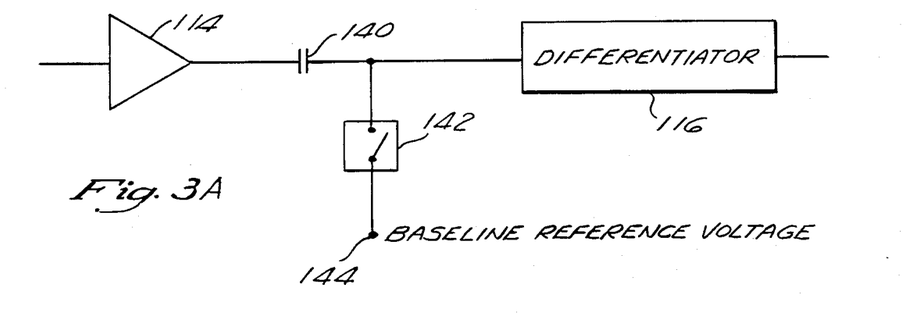
FIG. 3A is a block diagram that illustrates a preferred embodiment of the clamping portion of the present invention.
Figure 3B:
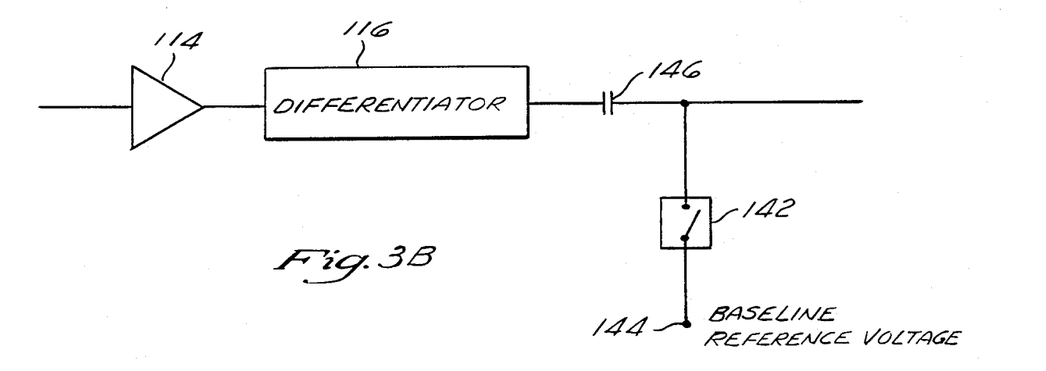
FIG. 3B is a block diagram that illustrates an alternative embodiment of the clamping portion of the present invention.

The general concept of the present invention is illustrated in FIGS. 3A and 3B. In FIG. 3A, the output of the differential amplifier 114 is capacitively coupled to the input of the differentiator 116 by a capacitor 140. The capacitor 140 couples the AC components of the signal output of the differential amplifier 114 to the input of the differentiator 116 and blocks the DC components of the signal. An electrically-controlled switch 142 is electrically connected between the input of the differentiator 116 and a baseline voltage reference 144. Although shown as a simple mechanical switch, it should be understood that the electrically-controlled switch 142 is an electronic switch that opens and closes in response to an electrical input signal. One embodiment of such a switch will be disclosed in more detail below.

When the electrically-controlled switch is open, the signal output of the differential amplifier 114 is coupled to the input of the differentiator 116. When the electrically-controlled switch is closed, the input of the differentiator is clamped to the voltage of the baseline voltage reference 144. The difference in the baseline voltage and the output voltage of the differential amplifier 114 appears as a voltage across the coupling capacitor 140. In FIG. 3A, the output of the differentiator 116 is the differentiated bioimpedance signal dZ/dt, and is provided as the input to the signal processing circuitry 120 (FIG. 1) or other circuitry, such as will be described below.

Figure 5A:
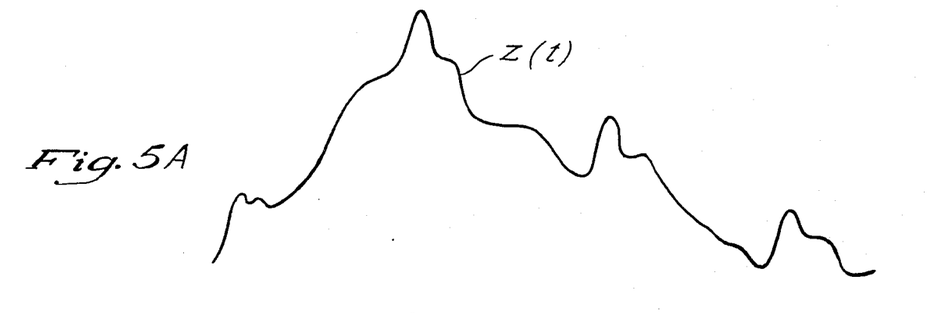
FIG. 5A is a graph of a typical electrical bioimpedance signal Z(t) modulated by the electrical bioimpedance signal caused by respiration (shown in dashed lines), also shown in FIG. 2C.
Figure 5B:
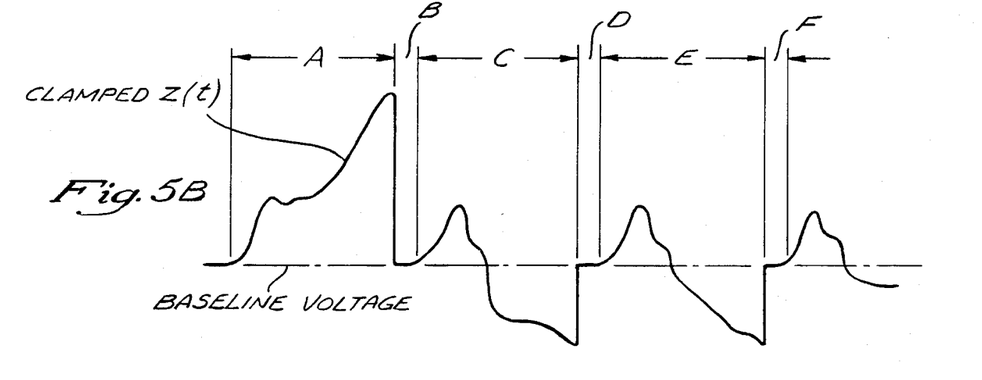
FIG. 5B is a graph of the signal shown in FIG. 5A as it would appear when clamping is of minimum duration.
Figure 5C:
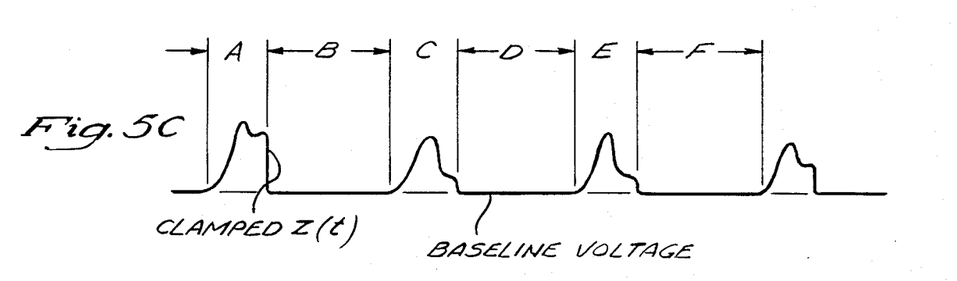
FIG. 5C is a graph of the signal shown in FIG. 5A as it would appear when clamping is of maximum duration.

The operation of the circuit in FIG. 3A is illustrated by the voltage waveforms in FIGS. 5A, 5B and 5C. The voltage waveform in FIG. 5A generally corresponds to the voltage waveform in FIG. 2C and represents the Z(t) output of the differential amplifier 114. As illustrated, the voltage waveform in FIG. 5A includes relatively large fluctuations caused by the combined effects of respiration combined with relatively small fluctuations caused by changes in blood flow during the cardiac cycle.

FIG. 5B illustrates the voltage waveform on the input of the differentiator 116 and demonstrates the effect of the electrically-controlled switch 142 on that voltage waveform when the electrically-controlled switch is closed for a short amount of time prior to the beginning of the mechanical systole of the heart. As illustrated in FIG. 5B, when the electrically controlled switch 142 is open, as during a time interval A, the voltage on the input of the differentiator 116 follows the voltage on the output of the differential amplifier 114. On the other hand, when the electrically-controlled switch 42 is closed, as during a time interval B, the voltage on the input of the differentiator 116 is clamped to the baseline voltage as shown. In FIG. 5B, the time interval B generally corresponds to the time from the occurrence of the QRS wave of the ECG signal to the beginning of mechanical systole. Thus, when the electrically-controlled switch 142 is again opened at the beginning of a time interval C, corresponding to the beginning of the mechanical systole of the heart, the voltage on the input of the differentiator 116 will begin changing from the baseline voltage and will be responsive to the fluctuations caused by the blood flow generated during the mechanical diastole of the heart. Thereafter, the voltage on the input of the differentiator 116 will change in accordance with the changes in the output voltage from the differential amplifier 114 until the electrically-operated switch is again closed during a time interval D. Thus, rather than the voltage on the input of the differentiator 116 following the extreme voltage swings of the output of the differential amplifier 114, it has relatively small voltage swings that begin at the baseline voltage and only change as much as the output voltage of the differential amplifier changes in one cardiac cycle. Time interval E again corresponds to a time when the electrically-controlled switch is open and time interval F corresponds to a time when the electrically-controlled switch is closed.

FIG. 5C illustrates a voltage waveform on the input of the differentiator 116 when the electrically-controlled switch 142 is closed throughout substantially all of the mechanical diastole portion of the cardiac cycle. Thus, the voltage on the input of the differentiator 116 is clamped to the baseline voltage at all times other than the mechanical systole portion of the heart cycle. This has the advantage of further suppressing the voltage swings applied to the input of the differentiator 116. In FIG. 5C, the time intervals A, C and E correspond to times when the electrically-controlled switch 142 is open and the time intervals B, D and F correspond to times when the electrically-controlled switch 142 is closed.

FIG. 3B illustrates an alternative circuit to the circuit in FIG. 3A. In FIG. 3B, the output of the differential amplifier 114 is connected directly to the input of the differentiator 116. On the other hand, the output of the differentiator 116 is not provided directly as an output. Rather, the output of the differentiator 116 is coupled through a coupling capacitor 146 to provide an AC-coupled output signal $dZ/dt_{OUT}$. In the embodiment of FIG. 3B, the AC-coupled output signal $dZ/dt_{OUT}$ is electrically connected to the electrically-controlled switch 144 that is connected to the baseline reference voltage 144, as before. In FIG. 3B, when the electrically-controlled switch 144 is open, the output of the differentiator 116 is coupled through the coupling capacitor 146 so that the AC-coupled output signal $dZ/dt_{OUT}$ tracks the output of the differentiator 116. When the electrically-controlled switch 144 is closed, the AC-coupled output signal dZ/dtOUT is clamped to the baseline reference voltage so that any changes in the voltage generated by the differentiator 116 appear across the coupling capacitor 146.

Figure 6A:
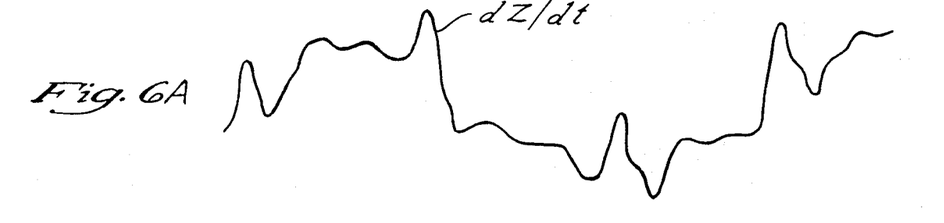
FIG. 6A is a graph of the differentiated electrical signal dZ/dt, also shown in FIG. 2D, which is the derivative of the electrical bioimpedance signal Z(t) shown in FIGS. 2C and 5A.
Figure 6B:
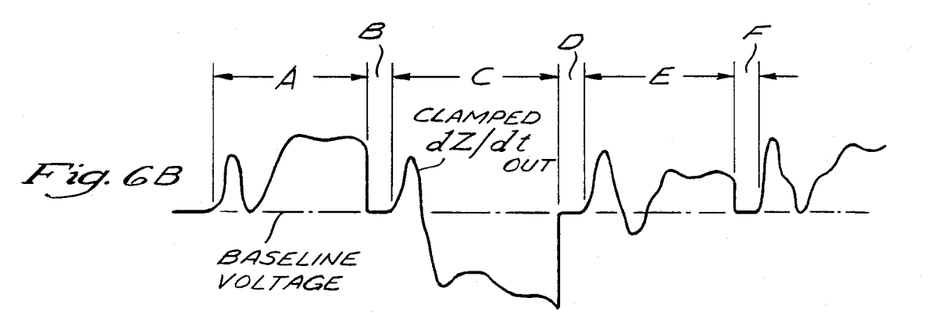
FIG. 6B is a graph of the signal shown in FIG. 5A as it would appear when clamping is of minimum duration.
Figure 6C:
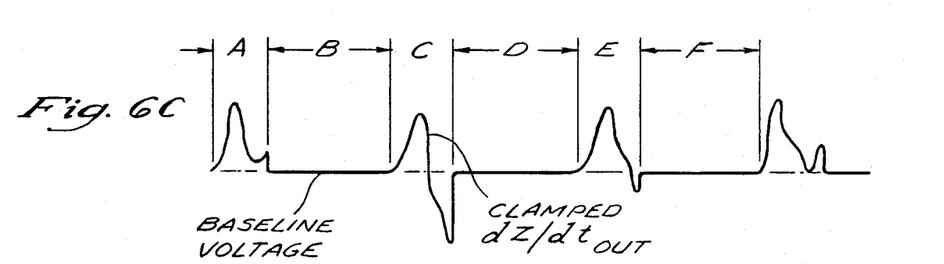
FIG. 6C is a graph of the signal shown in FIG. 5A as it would appear when clamping is of maximum duration.

The operation of the embodiment of FIG. 3B is illustrated in FIGS. 6A, 6B and 6C. FIG. 6A shows a typical differentiated electrical bioimpedance signal dZ/dt, for example, such as that provided as an output of the differentiator 116. As set forth above, the fluctuations of the differentiated electrical signal dZ/t are reduced compared to the fluctuations of the electrical bioimpedance signal Z(t); however, the dZ/dt signal has large low frequency voltage swings that are not completely suppressed by the differentiation. FIG. 6B shows the $dZ/dt_{OUT}$ signal after having passed through the coupling capacitor 146 and when being selectively clamped by the electrically-controlled switch 142. In FIG. 6B, the electrically-controlled switch 142 in the embodiment of FIG. 3B is closed from time of occurrence of the QRS portion of the ECG signal to the beginning of the mechanical systole of the cardiac cycle. Thus, the amplitude of the voltage of the $dZ/dt_{OUT}$ signal in FIG. 6B begins at the baseline reference voltage at the beginning of each mechanical systole. Time intervals A, C and E correspond to times when the electrically-controlled switch is open, and time intervals B, D and F correspond to times when the electrically-controlled switch is closed.

FIG. 6C illustrates the $dZ/dt_{OUT}$ signal when the electrically-controlled switch 142 is closed to clamp the $dZ/dt_{OUT}$ signal from the end of mechanical systole to the beginning of the next mechanical systole (i.e., throughout substantially all of the mechanical diastole). Clamping throughout mechanical diastole substantially reduces the voltage fluctuations in the $dZ/dt_{OUT}$ signal.

As set forth above, the present invention provides a novel apparatus and method for reducing or eliminating the effects of respiration in bioimpedance measurements by taking advantage of the fact that all of the desired information can be obtained during a reoccurring period of known duration. More specifically all of the desired data can be quantified during the mechanical systole of the heart. The undesirable effects of respiration are greatly reduced by clamping the bioimpedance signal or the differentiated bioimpedance signal to a baseline voltage level and holding it at the baseline voltage until just before commencement of the mechanical systole. The clamping provided by the present invention has the desirous effect of causing the electrical bioimpedance signal (FIGS. 5B and 5C) or the differentiated electrical bioimpedance signal (FIGS. 6B and 6C) to begin from a fixed base level at the beginning of each mechanical systole, thus reducing the extremes in the voltage changes in the electrical bioimpedance signal caused by respiration that occur randomly in relation to the cardiac cycle.

Figure 7:
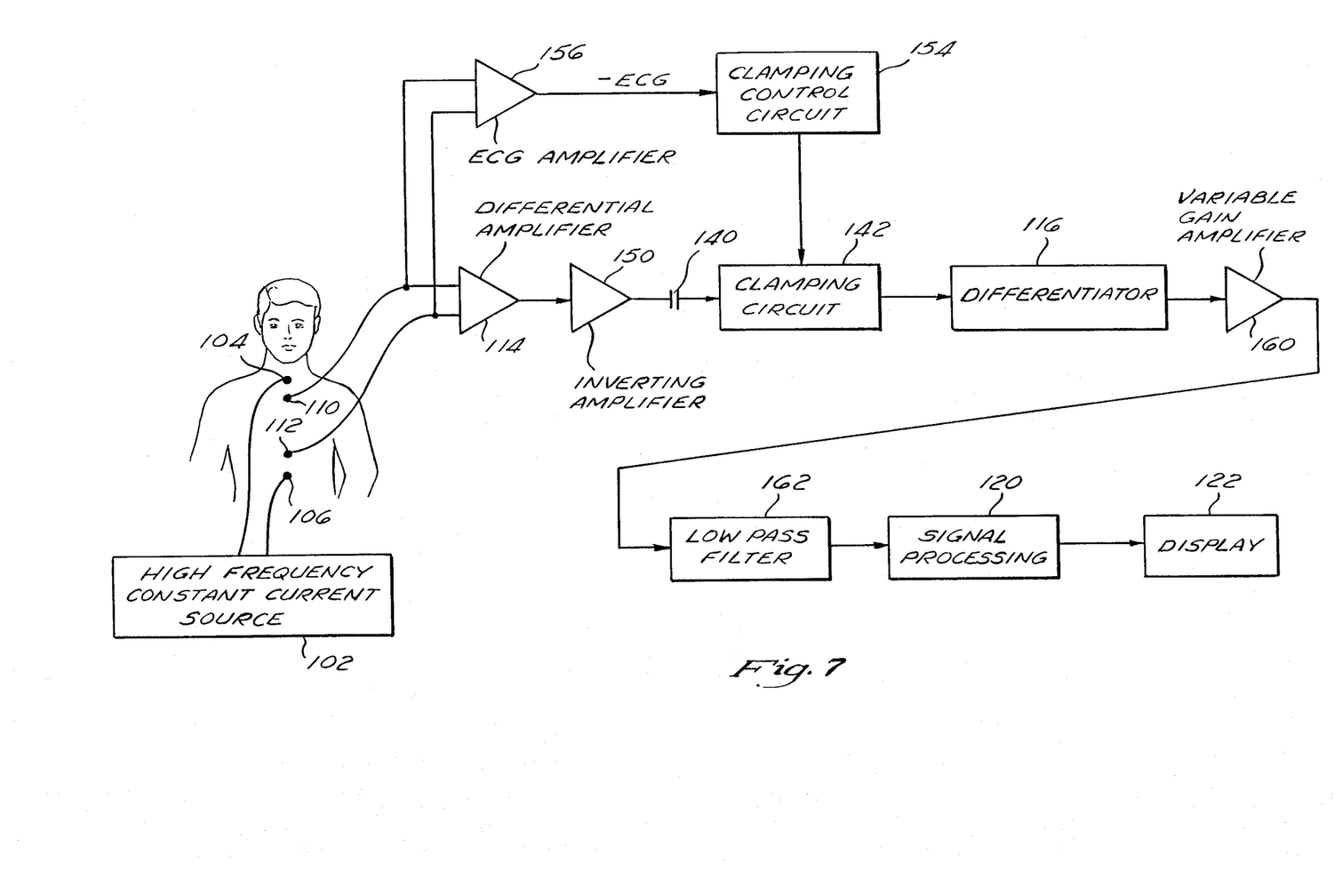
FIG. 7 is a block diagram illustrating a preferred embodiment of the invention.

The operation of the present invention when incorporated into an electrical bioimpedance system is further illustrated in block diagram form in FIG. 7. As explained above in relation to FIG. 1, a high frequency current source 102 is employed to create a voltage across the patient's thorax between sensing electrodes 110 and 112 by injecting current with the injecting electrodes 104 and 106. The voltage generated between the sensing electrodes 110 and 112 is detected by the differential amplifier 114 and further amplified by an inverting amplifier 150. The amplified electrical bioimpedance signal Z(t) is then coupled through the coupling capacitor 140 and through the clamping circuit 142 (i.e., the electrically-controlled switch 142) to the input of the differentiator 116.

The clamping circuit 142 is controlled by a clamping control circuit 154 that is synchronized by a -ECG signal generated by an ECG amplifier 156. The ECG amplifier 156 is electrically connected to the sensing electrodes 110, 112 and operates in a conventional manner to generate an amplified electrical signal having a negative maximum corresponding to the R-wave of the QRS complex of cardiac electrical activity. The R-wave causes the triggering of the clamping control circuit 154, as will be discussed below.

The output of the differentiator 116 is provided as an input to a variable gain amplifier 160. The variable gain amplifier 160 is adjusted so that 1 volt=1 ohm/second. In other words, a one-volt signal output from the variable gain amplifier 160 corresponds to a one-ohm per second rate of change in the electrical bioimpedance (dZ/dt=1 ohm/second). The variable gain amplifier 160 amplifies the differentiated electrical signal and outputs the amplified signal to a low pass filter 162. The low pass filter 162 has a cutoff frequency of approximately 30 Hz and removes 60 Hz noise associated with the supply line voltage along with other high frequency noise. The differentiated electrical signal dZ/dt is provided to the input of the processing circuit 120 so that the desired cardiac parameters can be determined and communicated to the operator by the visual display 122, or otherwise. Since the electrical bioimpedance signal Z(t) is clamped prior to the input of the differentiator 116, the signal provided as an input to the signal processing circuit 120 will not have the large voltage fluctuations that if would have if the clamping circuit were not present. In FIG. 7, the coupling capacitor 140 and the clamping circuit 142 are connected between the inverting amplifier 150 and the differentiator 116, corresponding to the embodiment of FIG. 3A. It should be understood that in an alternative embodiment (not shown) to the embodiment of FIG. 7, the coupling capacitor 140 and the clamping circuit 142 are interposed between the output of the differentiator 116 and the input of the variable gain amplifier 160, in accordance with FIG. 3B.

Figure 8:
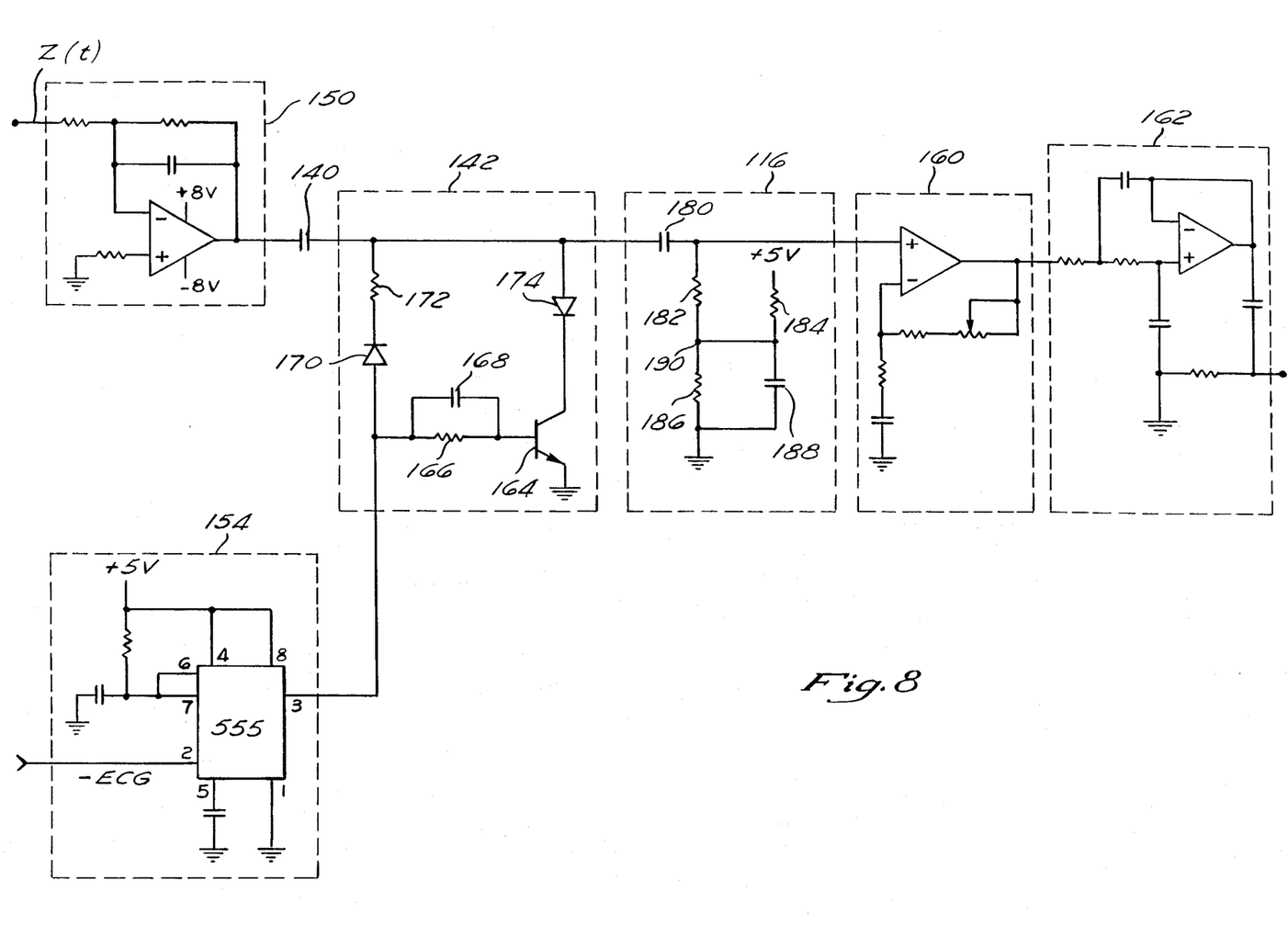
FIG. 8 is a detailed circuit diagram of a preferred embodiment of the electrical circuitry of the invention.

FIG. 8 is a detailed circuit diagram showing a preferred embodiment of the inverting amplifier 150, the coupling capacitor 140, the clamping circuit 142 (i.e., the electrically-controlled switch 142), the clamping control circuit 154, the differentiator 116, the variable gain amplifier 160, and the low pass filter 162. The inverting amplifier 150 is designed so as to have a selected gain A (e.g., A=−100). The electrical bioimpedance signal Z(t) output by the differential amplifier 114 (FIG. 6) is received by the inverting amplifier 150 and amplified in order to increase the amplitude of the signal to a usable value. The amplified electrical bioimpedance signal AZ(t) output by the inverting amplifier 150 is provided as an input to the clamping circuit 142 through the coupling capacitor 140. The clamping circuit 142 is controlled by the clamping control circuit 154 which, in the preferred embodiment, is advantageously a standard 555 timer connected for monostable operation. In the embodiment shown, the passive timing elements are selected so as to cause the 555 timer to have a triggered pulse duration of approximately 40 mS, approximately equal to the minimum duration of the PEP interval. The trigger for the clamping control circuit 154 is derived in a conventional manner from the R-wave of the QRS complex of the electrocardiogram of the patient's heart so that the pulse output of the clamping control circuit is active for approximately 40 mS after the beginning of the QRS wave. The electrical bioimpedance signal Z(t) is clamped during the 40 mS pulse duration of the clamping control circuit 154. Thus, in the embodiment shown, the clamping circuit 142 is active during most of the PEP interval and is released just prior to the beginning of the mechanical systole of the patient's heart. The clamping action corresponds to the clamping action described above in connection with FIG. 5B. The clamped and amplified electrical bioimpedance signal is then provided as an input to differentiator 116 which differentiates the clamped Z(t) signal and provides a differentiated output signal dZ/dt. The differentiated electrical signal dZ/dt is provided as an input to the variable gain amplifier 160. The variable gain amplifier 160 is adjusted such that each 1 ohm/second variation in the rate of change of the electrical bioimpedance signal Z(t) corresponds to a 1 volt variation at the output of the variable gain amplifier 160. The signal output of the variable gain amplifier 160 is then passed through the low pass filter 162 in order to remove any high frequency noise.

As set forth above, the electrically-controlled switch or clamping circuit 142 is an electronic switch that is controlled by the output of the 555 timer in the clamping control circuit 154. It should be understood that the voltage output of the inverting amplifier has both positive and negative voltage swings with respect to a circuit ground reference. Thus, the clamping circuit 142 must be able to clamp either polarity of voltage swing to the baseline voltage reference. A detailed description of the operation of an exemplary preferred embodiment of the clamping circuit 142 shown in FIG. 8. This particular embodiment advantageously clamps both the positive and negative output of the inverting amplifier 150. The amplified electrical bioimpedance signal AZ(t) generated by the inverting amplifier 150 is capacitively coupled to the clamping circuit 142 through the capacitor 140. While the output of the 555 timer in the clamping control circuit 154 is low (approximately 0.1 to 0.25 volts), no clamping occurs since transistor 164 is in cutoff and negligible current flows from the collector to the emitter of transistor 164. Furthermore, the diode 170 is reverse biased to prevent the diode 170 and the resistor 172 from effecting the amplified electrical bioimpedance signal.

When the ECG trigger causes the output of the clamping control circuit 154 to go high, its output will be approximately 4 volts. The voltage available at the base-emitter junction, after the voltage drop across the biasing resistor 166 and the capacitor 168, will cause the transistor 164 to saturate. The collector-emitter saturation voltage, $V_{ce(sat)}$, of the transistor 164 will be approximately equal to 0.2 volts and the voltage drop across the now forward biased diode 174 will be approximately 0.7 volts. Hence, during clamping, the voltage at the output of the clamping circuit 142 equals the sum of the voltages across the diode 174 and the collector-emitter junction of the transistor 164 and will be approximately 0.9 volts. Whenever the clamping circuit 142 is active, the diode 170 and the resistor 172 are operating as a relatively constant 7.9 mA current source to both the diode/transistor 174, 164 combination and the coupling capacitor 140 in order to maintain a constant 0.9 volts at the output of the clamping circuit 142. The current provided by the diode 170 and the resistor 172 is equal to the current through the resistor 172 which can be calculated using the following equation:

$$\frac{V_{555 \text{ Timer}} - V_{Diode} - 0.9 \text{ v}}{R_{172}}$$

where $V_{555}$ Timer is the high level output voltage of the 555 timer (e.g., approximately 4.0 volts), $V_{Diode}$ is the forward voltage drop of the diode 170 (e.g., approximately 0.7 volts) and $R_{172}$ is the resistance of the resistor 172 (e.g., 330 ohms). When the appropriate values are substituted for the above variables, the following is obtained:

$$\frac{4.0 \text{ v} - 0.7 \text{ v} - 0.9 \text{ v}}{330 \text{ Ohms}} = \frac{2.6 \text{ v}}{330 \text{ Ohms}} = 7.9 \text{ mA}$$

The output of the inverting amplifier 150 supplies the charging current to the coupling capacitor 140 when the amplified electrical bioimpedance signal AZ(t) is greater than 0.9 volts. In the event that the amplified electrical bioimpedance signal AZ(t) drops below 0.9 volts, the forward biased diode 170 and the resistor 172 will source the charging current required by the coupling capacitor 140. Hence, it can be seen from FIG. 8 and the description of the clamping circuit 142 herein, when the output of the clamping control circuit is high, the output of the clamping circuit will be a steady baseline voltage of approximately 0.9 volts.

By clamping one side of the coupling capacitor 140 to a baseline voltage of approximately 0.9 volts, any change in the electrical bioimpedance signal above or below that baseline voltage is stored across coupling capacitor 140. In other words, the amplitude of the electrical bioimpedance signal at the beginning of the mechanical systole, less the baseline voltage of approximately 0.9 volts, is caused to be stored across coupling capacitor 140 in opposite polarity in relation to the incoming electrical bioimpedance signal. When the clamping circuit 142 is released, the electrical bioimpedance signal is re-coupled to the differentiator 116 through coupling capacitor 140. Any variation in the electrical bioimpedance signal above or below the baseline voltage of 0.9 volts that is present just prior to release of the clamping circuit 142 is negated by that voltage variation having been stored across the coupling capacitor 140 when the clamping circuit 142 was active. The net result is that any changes in the electrical bioimpedance signal caused by respiration are suppressed except during the short period of time during which cardiac data is being quantified. Although he respiratory contribution is not suppressed during this short period of quantification, it is approximately a linear function and therefore can be removed by simple algorithmic means. Clamping the electrical bioimpedance signal to approximately 0.9 volts until just before the mechanical systole has the additional advantageous effect of preventing the respiratory signal, roughly an order of magnitude larger than the electrical bioimpedance signal due to cardiac activity, from driving the electronic circuitry (e.g. the differentiator 116 and the variable gain amplifier 160) out of its linear range.

In the embodiment illustrated in FIG. 8, the differentiator 116 includes a differentiating capacitor 180, a differentiating resistor 182, a first bias resistor 184, a second bias resistor 186 and a filter capacitor 188. The first bias resistor 184 and the second bias resistor 186 are connected in series between a DC power source (e.g., +5 volts) and a ground reference to provide a voltage divider network having a reference voltage (e.g., 1.56 volts) at a reference node 190 corresponding to the common connection between the two resistors 184, 186. The filter capacitor 188 is connected between the reference node 190 and the ground reference to substantially reduce or eliminate any noise at the reference node 190. The differentiating capacitor 180 has a first terminal connected to the output of the clamping circuit 142 and has a second terminal connected to the input of the variable gain amplifier 160. The differentiating resistor 182 has a first lead connected to the second terminal of the differentiating capacitor 180 and has a second lead connected to the reference node 190. The differentiating capacitor 180 and differentiating resistor 182 operate in a conventional manner to differentiate the signal output of the clamping circuit 142 and provide the differentiated output as the input to the variable gain amplifier 160. However, since the second lead of the differentiating resistor 182 is connected to the reference node 190 rather than the ground reference, the differentiated output signal is biased to a positive voltage with respect to ground so that for small voltage swings when the electrical bioimpedance signal is unclamped during mechanical systole the voltage applied to the input of the variable gain amplifier 160 is positive.

While the description focused on the clamping operation occurring before the differentiator 116, it should be appreciated that clamping can be implemented after the differentiator 116 as shown in FIG. 3B. Clamping the dZ/dt signal generated by the differentiator 116 has the same effect of reducing the voltage swing of the differentiated signal so that the electrical circuit operates within a limited voltage range during the mechanical systole of the heart.

As set forth above, the clamping circuit is operated so that the electrical bioimpedance signal is forced to the baseline voltage immediately prior to the beginning of the mechanical systole of the heart. Thus, although the electrical circuits may have been operating outside their linear ranges prior to the occurrence of the QRS wave, the operation of the clamping circuit brings all of the electrical signals following the clamping circuit within the linear range of the circuits prior to the beginning of the mechanical systole.

In an alternative embodiment not shown, the timing of the clamping control circuit 154 can be adjusted to maintain the differentiated electrical bioimpedance signal in the clamped condition except during a small window of time that begins before the mechanical systole and ends after the conclusion of mechanical systole. For example, two timing signals can be incorporated into the clamping control circuit. The first timing signal can be initiated by the occurrence of the QRS signal as set forth above and will have time duration substantially equal to the Pre-Ejection Period. At the conclusion of the first timing signal, a second timing signal is generated that opens the above-described clamping switch 142 for an amount of time substantially equal to the time duration of the mechanical systole of the heart. When the second timing signal concludes, the clamping switch 142 then closes until the beginning of the next mechanical systole. As set forth above, this embodiment has the advantage of suppressing the voltage swings except during the time when the bioimpedance signals are to be analyzed.

What is claimed is:

1. A non-invasive apparatus for measuring cardiac output of a patient, comprising:
   a bioimpedance measuring device that produces an electrical bioimpedance signal indicative of the thoracic impedance as a function of time;
   a differentiating circuit that receives a signal responsive to said electrical bioimpedance signal, and that differentiates said signal responsive to said electrical bioimpedance signal to generate a differentiated electrical signal indicative of the rate of change of thoracic impedance as a function of time; and
   a clamping circuit that periodically clamps said differentiated electrical signal to a fixed predetermined reference voltage so that said differentiated electrical signal is active only for a predetermined time duration following the beginning of each cardiac cycle.

2. The apparatus as defined in claim 1, wherein said bioimpedance measuring device comprises:
   a current source having a high frequency constant amplitude electrical current output;
   a pair of injector electrodes that inject the current output into a fist portion of a patient's body;
   a pair of sensor electrodes that sense a voltage across a second portion of the patient's body caused by current flow in said first portion of the patient's body; and
   an amplifier connected to said pair of sensor electrodes that receives said voltage and generates said electrical signal indicative of the thoracic impedance as a function of time.

3. The apparatus as defined in claim 1, wherein said clamping circuit comprises an electrically controlled switch, said switch being timed to be closed except during said predetermined time following the beginning of each cardiac cycle.

4. The apparatus as defined in claim 3, further including a timing circuit to control said switch, said timing circuit providing an output signal that controls the closing of said switch, said timing circuit responsive to the ECG output signals from the heart of the patient so that the operation of said switch is synchronized with the ECG output signals from the heart of the patient.

5. The apparatus as defined in claim 3, wherein said electrically controlled switch is located at the input of said differentiating circuit so that said electrically controlled switch clamps said signal responsive to said electrical bioimpedance signal.

6. The apparatus as defined in claim 3, wherein said electrically controlled switch is located at the output of said differentiating circuit.

7. A method of measuring the cardiac output of the heart of a patient comprising the steps of:
   applying a high frequency constant current to a first portion of the patient's body;
   sensing a voltage developed across a second portion of the patient's body caused by the flow of said high frequency constant current through said first portion;
   amplifying said sensed voltage;
   differentiating said sensed voltage to provide a differentiated output signal; and
   clamping said differentiated output signal to a fixed predetermined reference voltage for a predetermined amount of time during each cardiac cycle so that said differentiated output signal has a fixed magnitude during a selected time period prior to the mechanical systole of the patient's heart and has a variable magnitude corresponding to the rate of change of said sensed voltage during the mechanical systole of the heart.

* * * * *

UNITED STATES PATENT AND TRADEMARK OFFICE
CERTIFICATE OF CORRECTION

PATENT NO. : 4,870,578

DATED : September 26, 1989

INVENTOR(S) : Vlastimil Pat Vysin, et al.

It is certified that error appears in the above-identified patent and that said Letters Patent is hereby corrected as shown below:

```
In Column 7, at line 8, change "amplifier 1!4" to
     --amplifier 114--.
In Column 7, at line 24, change "switch 42 is" to --switch
     142 is.
In Column 8, at line 11, change "differentiator !16" to
     --differentiator 116--.
In Column 8, at line 15, change "dZ/dtOUT is" to --dZ/dt_{OUT}
     is--.
```

Signed and Sealed this

Twenty-first Day of April, 1992

Attest:

HARRY F. MANBECK, JR.

*Attesting Officer*   *Commissioner of Patents and Trademarks*